US00PP07783P

United States Patent [19]

Meilland

[11] Patent Number: Plant 7,783

[45] Date of Patent: Feb. 11, 1992

[54] ROSE PLANT—MEIPITAC VARIETY

[75] Inventor: Alain A. Meilland, Antibes, France

[73] Assignee: The Conard-Pyle Company, West Grove, Pa.

[21] Appl. No.: 580,190

[22] Filed: Sep. 10, 1990

[51] Int. Cl.[5] ..... A01H 5/00

[52] U.S. Cl. ..... Plt./1

[58] Field of Search ..... Plt. 1, 11, 12, 22

[56] References Cited

U.S. PATENT DOCUMENTS

| | | | |
|---|---|---|---|
| P.P. 3,525 | 3/1974 | Lammerts | Plt. 22 |
| P.P. 3,555 | 5/1974 | Warriner | Plt. 22 |
| P.P. 5,553 | 9/1985 | Olij | Plt. 22 |
| P.P. 7,139 | 2/1990 | Suzuki | Plt. 22 |

*Primary Examiner*—Howard J. Locker

*Attorney, Agent, or Firm*—Burns, Doane, Swecker & Mathis

[57] ABSTRACT

A new and distinct variety of shrub rose plant is provided which forms in abundance attractive bicolored blossoms which are China Rose on the upper surface and Cream White widely suffused with Pale Pink on the under surface. The petals are very consistent. The blossoms are well disposed on the plant and form a visually appealing contrast with bright dark green foliage. Very quick reflowering cycles are exhibited. A very well-balanced plant is formed which exhibits excellent disease resistance.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) of the new variety was the product of the cross between the Prairie Princess variety (nonpatented in the United States) and the Meirisouru variety (nonpatented in the United States). The Meirisouru variety sometimes is known as the Nirvana variety. The male parent (i.e., the pollen partent) of the new variety was the product of the cross of the Maceye variety (U.S. Plant Pat. No. 3,985) and the Meivilanic variety (nonpatented in the United States). The Maceye variety sometimes is known as the Eye Paint variety. The parentage of the new variety can be summarized as follows:

(Prairie Princess × Meirisouru) × (Maceye × Meivilanic).

The seeds resulting from the above pollination were sown and 38 plantlets were obtained which were physically and biologically different from each other. Selective study resulted in the identification of a single plant of the new variety.

It was found that the new variety of shrub rose plant of the present invention possesses the following combination of characteristics:

(a) abundantly and continuously forms attractive long lasting double bicolored blossoms which are China Rose on the upper surface and Cream White widely suffused with Pale Pink on the under surface,
(b) forms blossoms having very consistent petals,
(c) exhibits a very rapid reflowering cycle,
(d) forms vigorous vegetation,
(e) assumes a well-balanced configuration,
(f) forms bright dark green foliage, and
(g) is not particularly affected by cryptogamic diseases.

The blooms are disposed very nicely on the plant.

The new variety well meets the needs of the horticultural industry. It can be grown to advantage as an attractive ornamentation in parks, gardens, public areas, and residential landscapes. Accordingly, it is particularly well suited for growing in the landscape.

Asexual propagation by conventional methods such as budding, grafting, and cuttage as performed in France show that the characteristics of the new variety are homogeneous and stable and are strictly transmissible from one generation to another.

The new variety has been named the Meipitac variety.

BRIEF DESCRIPTION OF THE PHOTOGRAPH

The accompanying photograph shows, as nearly true as it is reasonably possible to make the same in a color illustration of this character, typical specimens of plant parts of the new variety. The rose plants of the new variety described herein were three years of age and were grown outdoors during June while budded on *Rosa froebelli* understock at LeCannet-des-Maures, Var, France.

DETAILED DESCRIPTION

Figures 1, 2, 3, 4, 5, 6, 7, 8, 9, 10, 11, 12, 13, 14, 15, 16:
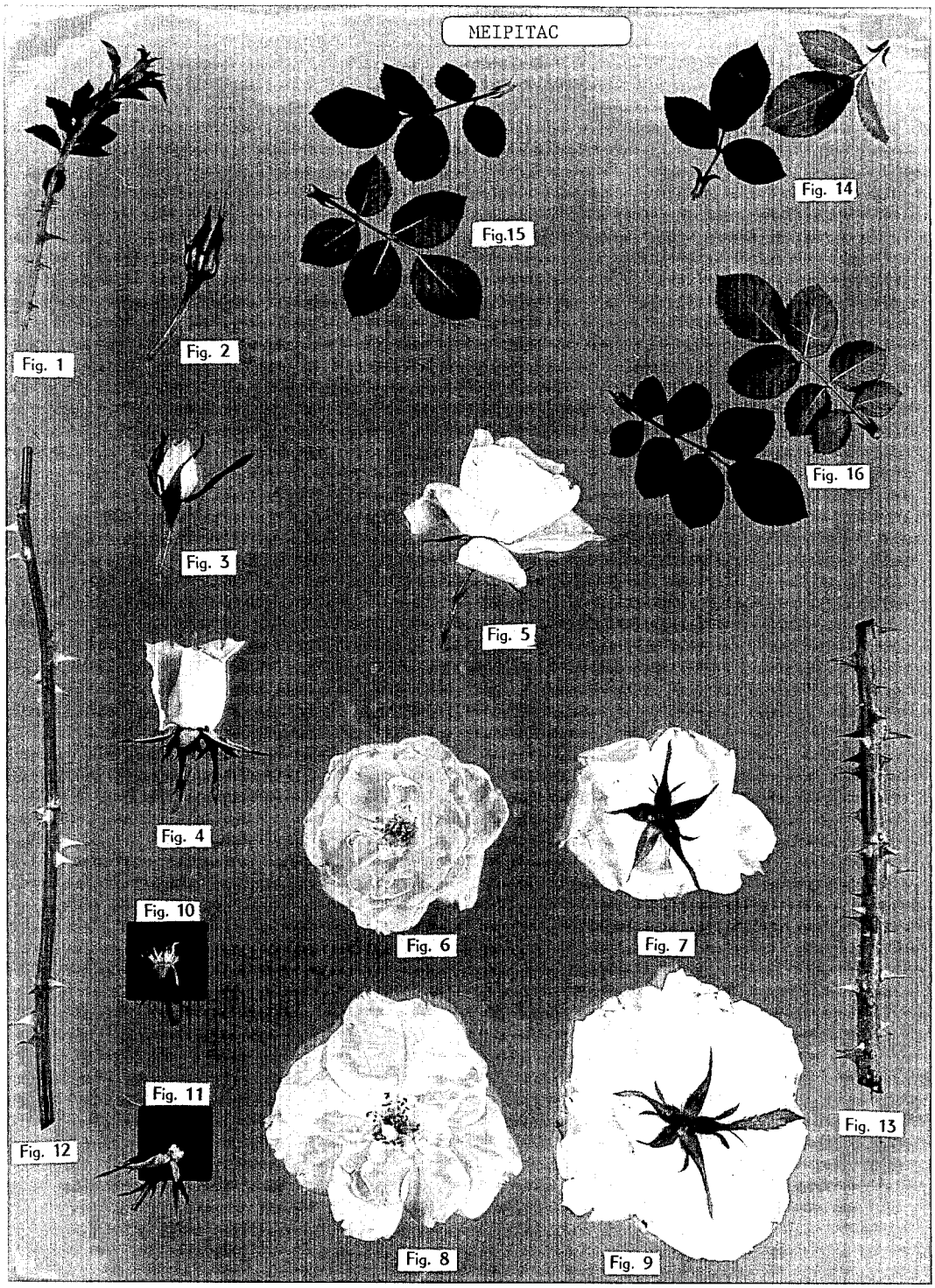
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud as the petals open.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets — plan view — obverse (left) and reverse (right)
FIG. 15 illustrates specimens of leaves with five leaflets — plan view — obverse (top) and reverse (bottom)
FIG. 16 illustrates specimens of leaves with seven leaflets — plan view — obverse (lower left) and reverse (upper right).

The chart used in the identification of colors is that of The Royal Horticultural Society (R.H.S. Colour Chart). The terminology which precedes reference to the chart has been added to indicate the corresponding color in more common terms. The description is based on three-year old specimens of the new variety during June while budded on *Rosa froebelli* understock and grown outdoors at LeCannet-des-Maures, Var, France.

Class: Shrub.

Plant: *Height.*—Approximately 100 to 120 cm. on average.

*Habit.*—Bushy.

Branches:

*Color.*—Young stems: light green, Yellow-Green Group 146D. Adult wood. medium green, Yellow-Green Group 146B.

*Thorns.*—Size: medium to small. Quantity: numerous to moderately numerous. Color: pinkish with greenish tips on young stems and greenish changing to light tan on adult wood.

Leaves:

*stipules.*—Adnate, pectinate, wide and linear.

*Petioles.*—Upper surface: striped, reddish-brown on young foliage, medium green on mature foliage with more or less glandular edges. Under surface: light green and bear only a few prickles.

*Leaflets.*—Number: 3, 5 (most often), and 7. Shape: oval. Serration: single and regular. Texture: leathery. Overall appearance: dense and bright foliage. Color (young foliage): Upper surface: light green, Yellow-Green Group 146C, widely suffused with reddish coloration. Under surface: reddish brown. Color (adult foliage): Upper surface: dark green, Yellow-Green Group 147A. Under surface: medium green, Green Group 137B.

Inflorescence:

*Number of flowers.*—Approximately 1 to 3 blooms per floral stem.

*Penduncle.*—Medium green, more or less stained with reddish coloration, with more or less glandular edges, and approximately 6 to 7 cm.

*Sepals.*—Upper surface: tomentose and greenish. Under surface: light green, more or less tinged with reddish coloration, and the outer sepals have more or less appendiculated edges which terminate in a more or less developed leaf-like appendix.

*Buds.*—Shape: ovoid. Length: approximately 2.5 on average. Size: medium. Color (when opening): Upper surface: Rose Bengal, Red-Purple Group 57B. Under Surface: Cream White, Yellow-White Group 158D, very widely suffused with Pale Pink, Red Group 56D, and shaded with spots of light Rose Bengal, Red-Purple Group 57C.

*Flower.*—Form: cuplike, double. Diameter: approximately 10 to 11 cm. on average. Color (when opening begins): Upper surface: Rose Bengal, Red-Purple Group 57B. Under surface: Cream White, Yellow-White Group 158D, very widely suffused with Pale Pink, Red Group 56D, and more or less shaded with spots of light Rose Bengal, Red-Purple Group 57C. Color (when blooming): Upper surface: China Rose, Red-Purple Group 58B, lighter and turning white on the outer petals. Under surface: Cream White, Yellow-White Group 158D, widely suffused with Pale Pink, Red Group 56D, and lightly shaded with light Red Bengal, Red-Purple Group 57C. Color (at end of blooming): Upper surface: China Rose, Red-Purple Group 58B, lighter and turning white on the outer petals. Under surface: Cream White, Yellow-White Group 158D, slightly suffused with Light Pink, Red Group 56D. Fragrance: slight. Flower duration: long. Petal form: oval. Petal texture: very consistent. Petal number: approximately 30 on average. Petal drop: very good. Stamen number: approximately 63 on average. Anthers: light ochre, very elongated. Filaments greenish in coloration, long, and of irregular heights. Pistils: approximately 25 to 30 on average. Stigmas: greenish straw colored. Styles: straw colored, more or less twisted and tomentose at the base, of irregular heights. Receptacle: smooth, light green, and in longitudinal section it is narrow and in the shape of a pitcher.

Development:

*Vegetation.*—Strong.

*Blossoming.*—Very floriferous, continuous, has a very quick flowering cycle.

*Aptitude to bear fruits.*—Good.

*Resistance to frost.*—Excellent.

*Resistance to Diseases.*—Excellent.

I claim:

1. A new and distinct variety of rose plant of the Shrub Class characterized by the following combination of characteristics:

(a) abundantly and continuously forms attractive long lasting double bicolored blossoms which are China Rose on the upper surface and Cream White widely suffused with Pale Pink on the under surface,
(b) forms blossoms having very consistent petals,
(c) exhibits a very rapid reflowering cycle,
(d) forms vigorous vegetation,
(e) assumes a well-balanced configuration,
(f) forms bright dark green foliage, and
(g) is not particularly affected by cryptogamic diseases;

substantially as herein shown and described.

* * * * *

MEIPITAC